United States Patent
Peng et al.

(10) Patent No.: US 10,450,328 B2
(45) Date of Patent: Oct. 22, 2019

(54) CRYSTALS OF THIADIAZOLE DERIVATIVE DPP-IV INHIBITORS AND USES THEREOF

(71) Applicants: CHIA TAI TIANQING PHARMACEUTICAL GROUP CO., LTD., Lianyungang (CN); CENTAURUS BIOPHARMA CO., LTD., Beijing (CN)

(72) Inventors: Yan Peng, Lianyungang (CN); Fei Liu, Lianyungang (CN); Zhilin Chen, Lianyungang (CN); Yayu Zhang, Lianyungang (CN); Zhongyuan Hu, Lianyungang (CN); Jinfeng Jiang, Lianyungang (CN)

(73) Assignees: Chia Tai Tianqing Pharmaceutical Group Co., Ltd. (CN); Centaurus Biopharma Co., Ltd. (CN)

( * ) Notice: Subject to any disclaimer, the term of this patent is extended or adjusted under 35 U.S.C. 154(b) by 0 days.

(21) Appl. No.: 15/779,420

(22) PCT Filed: Nov. 24, 2016

(86) PCT No.: PCT/CN2016/107076
§ 371 (c)(1),
(2) Date: May 25, 2018

(87) PCT Pub. No.: WO2017/088790
PCT Pub. Date: Jun. 1, 2017

(65) Prior Publication Data
US 2018/0334466 A1    Nov. 22, 2018

(30) Foreign Application Priority Data

Nov. 27, 2015 (CN) .......................... 2015 1 0845342

(51) Int. Cl.
*C07D 519/00* (2006.01)
*A61K 31/522* (2006.01)
*A61P 3/10* (2006.01)

(52) U.S. Cl.
CPC .......... *C07D 519/00* (2013.01); *A61K 31/522* (2013.01); *A61P 3/10* (2018.01); *C07B 2200/13* (2013.01)

(58) Field of Classification Search
None
See application file for complete search history.

(56) References Cited

FOREIGN PATENT DOCUMENTS

CN    102807568 A    12/2012

OTHER PUBLICATIONS

Caira, Mino R., "Crystalline Polymorphism of Organic Compounds," Department of Chemistry, University of Cape Town, Rondebosch 7700, South Africa, Topics in Current Chemistry, vol. 198, Springer Verlag, Berlin Heidelberg, 1998, 46 pages.
Extended European Search Report dated Aug. 16, 2018 in EP Application No. 16868013.0.
International Search Report dated Feb. 6, 2017 issued in Application No. PCT/CN2016/107076.

*Primary Examiner* — Po-Chih Chen
(74) *Attorney, Agent, or Firm* — Weaver Austin Villeneuve & Sampson LLP

(57) ABSTRACT

The present invention belongs to the field of drug crystals, relates to crystals of thiadiazole derivative DPP-IV inhibitors, and in particular relates to A and B type crystals of the compound as shown in formula 7. The crystals of the present invention have excellent stability. For example, under high temperature, high humidity or light test conditions, the material contents associated with the crystal of the compound of formula 7 do not change significantly. In addition, the crystal of the present invention also has a very good powder flowability and satisfies the requirements of drug preparation and production.

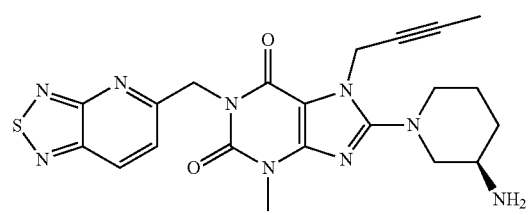

20 Claims, 3 Drawing Sheets

CRYSTALS OF THIADIAZOLE DERIVATIVE DPP-IV INHIBITORS AND USES THEREOF

CROSS REFERENCE TO RELATED APPLICATION

The present application claims priority to and the benefit of the Chinese patent application No. 201510845342.8 filed with the State Intellectual Property Office of China on Nov. 27, 2015, which is incorporated herein by reference in its entirety.

TECHNICAL FIELD

The present invention belongs to the field of medical chemistry, and specifically relates to crystals of thiadiazole derivative DPP-IV inhibitors, crystalline compositions, pharmaceutical compositions, and preparation methods and uses thereof.

BACKGROUND

DPP-IV (Dipeptidyl Peptidase IV) is a serine protease that is expressed in various tissues (such as liver, lung, intestine, kidney, etc.) in the body, and is responsible for the metabolic cleavage of endogenous peptides (GLP-1 (7-36)) in vivo. However, GLP-1 (7-36) has a variety of beneficial effects in the body, including the stimulation of insulin secretion, the inhibition of glucagon secretion, the promotion of satiety, and the delay of gastric emptying, etc. Hence, the inhibition of DPP-IV can be used to prevent and/or treat diabetes, particularly type II diabetes. At present, there are a variety of DPP-IV inhibitors on the market already, such as alogliptin, sitagliptin, saxagliptin, vildagliptin, linagliptin and so on.

Chinese Patent Application CN102807568 discloses a thiadiazole derivative DPP-IV inhibitor represented by Formula I or Formula II. The compounds of the formulas (especially Compound 7) have a very good inhibitory activity against DPP-IV. In addition, Compound 7 also has a very good metabolic level in vivo and a suitable half-life in vivo, and is particularly suitable as a DPP-IV inhibitor drug.

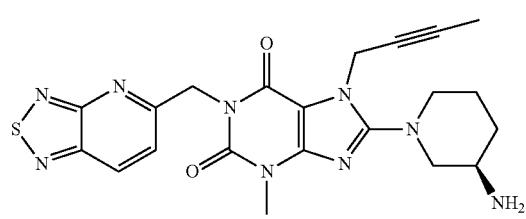

In addition to therapeutic efficacy, drug developers attempt to provide a suitable form of an active molecule having properties (e.g., processing, preparation, storage stability, etc.) as a drug. Therefore, it is also essential for drug development to find the form having desired properties.

SUMMARY OF THE INVENTION

In one aspect, the present invention provides a crystalline Form A of the compound represented by Formula 7:

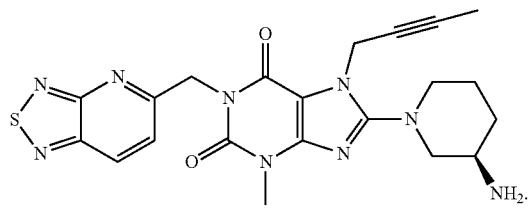

The crystalline Form A has diffraction peaks at about 6.54, 8.27 and 11.68 degrees 2θ in an X-ray powder diffraction (XRD) pattern using Cu-Kα radiation; typically has diffraction peaks at about 6.54, 8.27, 8.67, 9.16, 9.55, 11.68, 12.17, 12.98, 16.23, 18.15 and 18.91 degrees 2θ; and further typically has diffraction peaks at about 6.54, 8.27, 8.67, 9.16, 9.55, 10.80, 11.68, 12.17, 12.98, 14.35, 15.05, 15.64, 16.23, 16.73, 17.31, 18.15, 18.91, 19.43, 20.23, 20.79, 21.36, 23.25, 23.96, 24.53, 25.05, 26.54, 28.43, 29.63 and 30.19 degrees 2θ.

In one specific embodiment of the present invention, the XRD pattern of the crystalline Form A of the compound represented by Formula 7 has the following characteristics:

| No. | 2θ(°) | Relative Intensity (%) |
|---|---|---|
| 1 | 6.54 | 73 |
| 2 | 8.27 | 68 |
| 3 | 8.67 | 21 |
| 4 | 9.16 | 23 |
| 5 | 9.55 | 24 |
| 6 | 10.80 | 16 |
| 7 | 11.68 | 100 |
| 8 | 12.17 | 26 |
| 9 | 12.98 | 33 |
| 10 | 14.35 | 7 |
| 11 | 15.05 | 10 |
| 12 | 15.64 | 18 |
| 13 | 16.23 | 21 |
| 14 | 16.73 | 14 |
| 15 | 17.31 | 14 |
| 16 | 18.15 | 21 |
| 17 | 18.91 | 23 |
| 18 | 19.43 | 14 |
| 19 | 20.23 | 24 |
| 20 | 20.79 | 21 |
| 21 | 21.36 | 21 |
| 22 | 23.25 | 34 |
| 23 | 23.96 | 55 |
| 24 | 24.53 | 30 |
| 25 | 25.05 | 20 |
| 26 | 26.54 | 30 |
| 27 | 28.43 | 28 |
| 28 | 29.63 | 15 |
| 29 | 30.19 | 8 |

In one specific embodiment of the present invention, the crystalline Form A of the compound represented by Formula 7 has a powder X-ray diffraction pattern substantially as shown in FIG. 1.

In a further aspect, the present invention provides a method for preparing the crystalline Form A of the compound represented by Formula 7, comprising the following steps: a) dissolving the amorphous compound of Formula 7 in an appropriate amount of ethanol and heating the resulting mixture to 75-80° C. to obtain a clear solution, then adding an appropriate amount of activated carbon, and stirring the resulting mixture for 1-2 hours followed by filtration; b) gradually cooling the filtrate to 10-20° C. at a rate of 5° C. per hour, and then continuously stirring it for 5-7 hours; and c) filtering the resulting mixture, and drying the filter cake under vacuum at 45-55° C. for 5-7 hours.

In another aspect, the present invention provides a crystalline Form B of the compound represented by Formula 7, which has diffraction peaks at about 4.86, 6.24, 7.88, 10.54, 12.16, 15.82 and 23.70 degrees 2θ in an X-ray powder diffraction (XRD) pattern using Cu-Kα radiation; typically has diffraction peaks at about 4.86, 6.24, 7.88, 9.48, 10.54, 12.16, 15.82, 17.16, 17.76, 20.94 and 23.70 degrees 2θ; and further typically has diffraction peaks at about 4.86, 6.24, 7.88, 9.48, 10.54, 12.16, 12.54, 14.00, 14.68, 15.30, 15.82, 17.16, 17.76, 18.16, 19.16, 19.58, 20.94, 22.96, 23.70, 24.76, 25.70, 26.44, 28.02, 28.96 and 29.38 degrees 2θ.

In one specific embodiment of the present invention, the XRD pattern of the crystalline Form B of the compound represented by Formula 7 has the following characteristics:

| No. | 2θ(°) | Relative Intensity (%) |
|-----|-------|------------------------|
| 1   | 4.86  | 20                     |
| 2   | 6.24  | 100                    |
| 3   | 7.88  | 23                     |
| 4   | 9.48  | 13                     |
| 5   | 10.54 | 36                     |
| 6   | 12.16 | 28                     |
| 7   | 12.54 | 14                     |
| 8   | 14.00 | 23                     |
| 9   | 14.68 | 13                     |
| 10  | 15.30 | 23                     |
| 11  | 15.82 | 48                     |
| 12  | 17.16 | 25                     |
| 13  | 17.76 | 23                     |
| 14  | 18.16 | 15                     |
| 15  | 19.16 | 25                     |
| 16  | 19.58 | 25                     |
| 17  | 20.94 | 19                     |
| 18  | 22.96 | 40                     |
| 19  | 23.70 | 84                     |
| 20  | 24.76 | 32                     |
| 21  | 25.70 | 35                     |
| 22  | 26.44 | 23                     |
| 23  | 28.02 | 33                     |
| 24  | 28.96 | 16                     |
| 25  | 29.38 | 26                     |

In one specific embodiment of the present invention, the crystalline Form B of the compound represented by Formula 7 has a powder X-ray diffraction pattern substantially as shown in FIG. 2.

In a further aspect, the present invention provides a method for preparing the crystalline Form B of the compound represented by Formula 7, comprising the following steps: a) dissolving the amorphous compound of Formula 7 in an appropriate amount of ethyl acetate, isopropanol or isopropyl ether, heating the resulting mixture to 70-80° C. and stirring it for 1-2 hours; b) gradually cooling the resulting mixture to 10-20° C. at a rate of 5° C. per hour, and then continuously stirring it for 5-7 hours; and c) filtering the resulting mixture, and drying the filter cake under vacuum at 45-55° C. for 5-7 hours.

In another aspect, the present invention provides a crystalline composition comprising the crystalline Form A or the crystalline Form B as described above.

The crystalline composition comprising the crystalline Form A refers to a composition where the crystalline Form A accounts for 50% or more, preferably 80% or more, more preferably 90% or more, and most preferably 95% or more by weight of the composition. The composition may comprise a small amount of other crystalline or amorphous form of the compound of Formula 7, for example, including but not limited to, the crystalline Form B or an amorphous form of the compound of Formula 7.

The crystalline composition comprising the crystalline Form B refers to a composition where the crystalline Form B accounts for 50% or more, preferably 80% or more, more preferably 90% or more, and most preferably 95% or more by weight of the composition. The composition may comprise a small amount of other crystalline or amorphous form of the compound of Formula 7, for example, including but not limited to, the crystalline Form A or an amorphous form of the compound of Formula 7.

In a further aspect, the present invention provides a pharmaceutical composition comprising the crystalline forms or the crystalline composition as described above. Optionally, the pharmaceutical composition may further comprise pharmaceutically acceptable adjuvant(s). The pharmaceutically acceptable adjuvant(s) are well known to those skilled in the art, for example, the common adjuvants listed in "Pharmaceutics", 6$^{th}$ edition, edited by Fude Cui.

In another aspect, the present invention provides a method for inhibiting DPP-IV, comprising contacting the DPP-IV with the crystalline Form A, the crystalline Form B, the crystalline composition, or the pharmaceutical composition according to the present invention.

In still another aspect, the present invention provides a method for treating a disease benefiting from DPP-IV inhibition, comprising administering to a subject in need thereof the crystalline Form A, the crystalline Form B, the crystalline composition, or the pharmaceutical composition according to the present invention. Preferably, the disease is selected from diabetes. More preferably, the disease is selected from type II diabetes.

The term "subject" includes humans and animals, for example, mammals (such as primates, cattle, horses, pigs, dogs, cats, mice, rats, rabbits, goats, sheep and birds).

In yet another aspect, the present invention provides use of the crystalline Form A, the crystalline Form B, the crystalline composition, or the pharmaceutical composition according to the present invention in the preparation of a medicament for the treatment of a disease benefiting from DPP-IV inhibition. Preferably, the disease is selected from diabetes. More preferably, the disease is selected from type II diabetes.

In another aspect, the present invention provides the crystalline Form A, the crystalline Form B, the crystalline composition, or the pharmaceutical composition according to the present invention for use in the inhibition of DPP-IV.

In still another aspect, the present invention provides the crystalline Form A, the crystalline Form B, the crystalline composition, or the pharmaceutical composition according to the present invention for use in the treatment of a disease benefiting from DPP-IV inhibition.

Both the crystalline Form A and the crystalline Form B of the present invention have excellent stability. For example, under the experimental conditions of high temperature, high humidity, or light irradiation, the content of the relative substances in the crystalline forms of the compound of Formula 7 does not change significantly. In addition, the crystalline Form A and the crystalline Form B of the present invention also have good powder fluidity, and thus meet the requirements for the preparation and production of drugs.

SPECIFIC EMBODIMENTS

Figure 1:
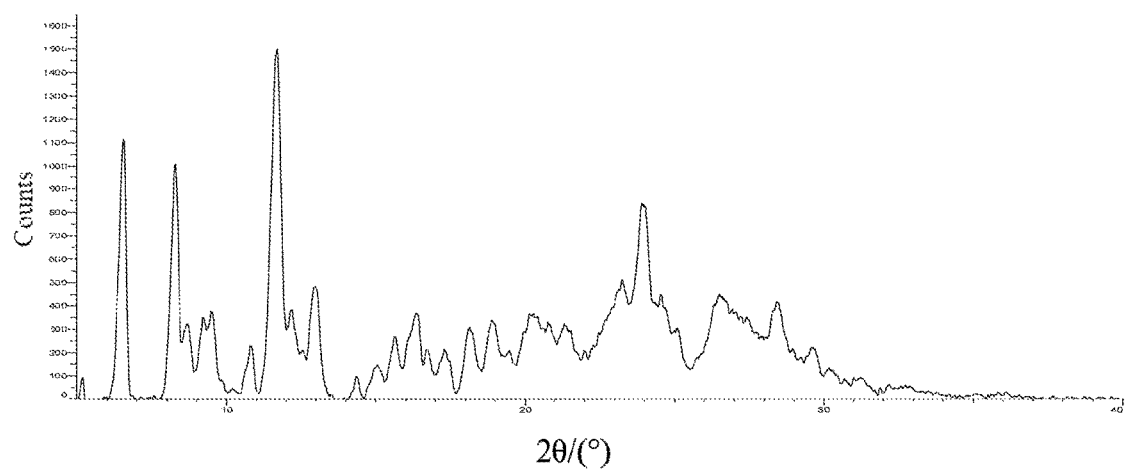
FIG. 1: an X-ray powder diffraction pattern of the crystalline Form A of the compound of Formula 7.

The present invention will be further illustrated with reference to the following examples, which enable those skilled in the art to more fully understand the present invention. They should not be construed as limiting the scope of the present invention, but as merely illustrations and typical representatives of the present invention.

Example 1: Preparation of the Amorphous Form of the Compound of Formula 7

The amorphous form of the compound of Formula 7 can be prepared with reference to the method described in Example 7 of CN102807568A.

The amorphous form of the compound of Formula 7 can also be prepared according to the method described below.

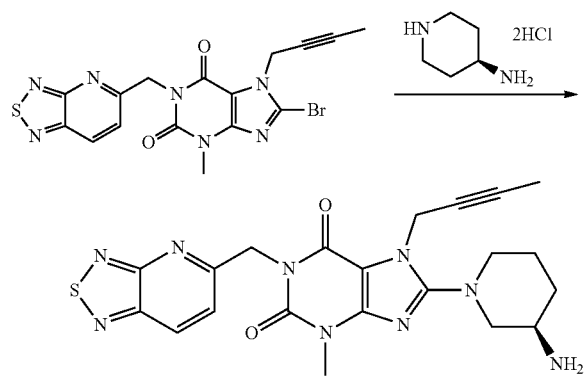

Intermediate 1

Under nitrogen protection, to a 30 L glass reaction vessel were added 5.5 L of ethanol, 550 g of Intermediate 1, 256 g of (R) 3-aminopiperidine dihydrochloride, and 414 g of sodium bicarbonate. The resulting mixture was stirred, heated to raise its temperature, and kept at a temperature of 75° C.-80° C., and stirred to react for 4 h. TLC (using 254 nm UV lamp to develop color, methanol:dichloromethane: ammonia=1:10:0.1, Rf Intermediate 1=0.7, Rf product=0.5) was monitored until Intermediate 1 was completely reacted. The resulting mixture was filtered, and the filter cake was washed with ethanol. The filtrate was evaporated to dryness under reduced pressure at 45±5° C., and then the residue was dissolved in 5 L of dichloromethane and washed with 5 L of purified water. Then, the resulting mixture was extracted and separated by adding 5 L of purified water and 288 g of citric acid, and 2.5 L of purified water was used to strip the organic phase and the aqueous phases were combined. The combined aqueous phase was washed with 5 L of dichloromethane and 10 L of ethanol, and then 5 L of dichloromethane was added thereto and the temperature was controlled to not higher than 30° C. A sodium hydroxide solution was slowly added to extract and separate the resulting mixture. The organic phase was washed with 5 L of purified water and then dried over anhydrous sodium sulfate. After filtration, the filtrate was evaporated to dryness under reduced pressure at 30±5° C. to obtain 372 g of the compound of Formula 7 as a solid in an amorphous form.

Figure 3:
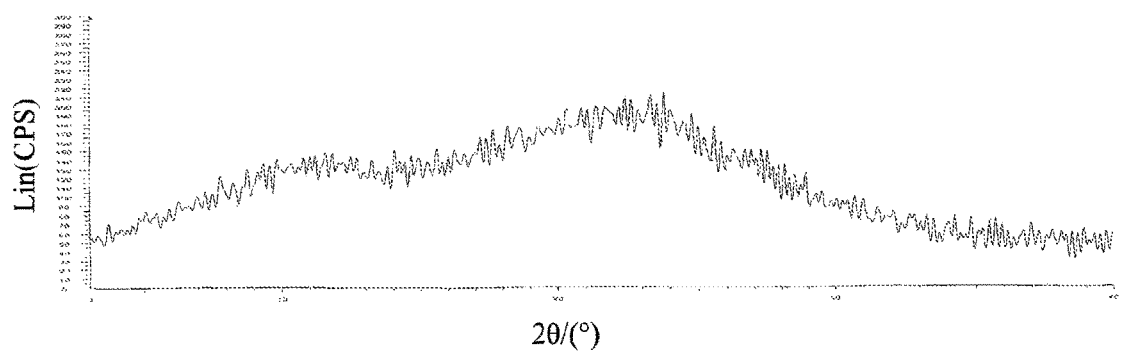
FIG. 3: an X-ray powder diffraction pattern of an amorphous form of the compound of Formula 7.

The X-ray powder diffraction pattern of the amorphous form of the compound of Formula 7 was shown in FIG. 3.

Example 2: Preparation of the Crystalline Form A of the Compound of Formula 7

250 g of the amorphous form of the compound of Formula 7 and 1.25 L of ethanol were added to a 2.5 L three-neck flask, and heated to 75-80° C. to obtain a clear solution. 12.5 g of activated carbon was added thereto, and the resulting mixture was stirred for 1 hour and then filtered under pressure into a 2.5 L three-necked flask. The filtrate was gradually cooled at a rate of 5° C. per hour, and kept at a temperature of 10-20° C. and stirred for 6 hours. After filtration, the filter cake was dried under vacuum at 50±5° C. for 6 h to obtain 151 g of a yellow powder, HPLC: 98.5%, yield 60.4%.

The X-ray powder diffraction pattern of the crystalline Form A of the compound of Formula 7 was shown in FIG. 1.

Example 3: Preparation of the Crystalline Form B of the Compound of Formula 7

250 g of the amorphous form of the compound of Formula 7 and 2.5 L of ethyl acetate were added to a 2.5 L three-neck flask, heated to 70° C. and then stirred for 2 hour. The resulting mixture was gradually cooled at a rate of 5° C. per hour, and kept at a temperature of 10-20° C. and stirred for 6 hours. After filtration, the filter cake was dried under vacuum at 50±5° C. for 6 h to obtain 137 g of a yellow powder, HPLC: 98.5%, yield 55%.

Figure 2:
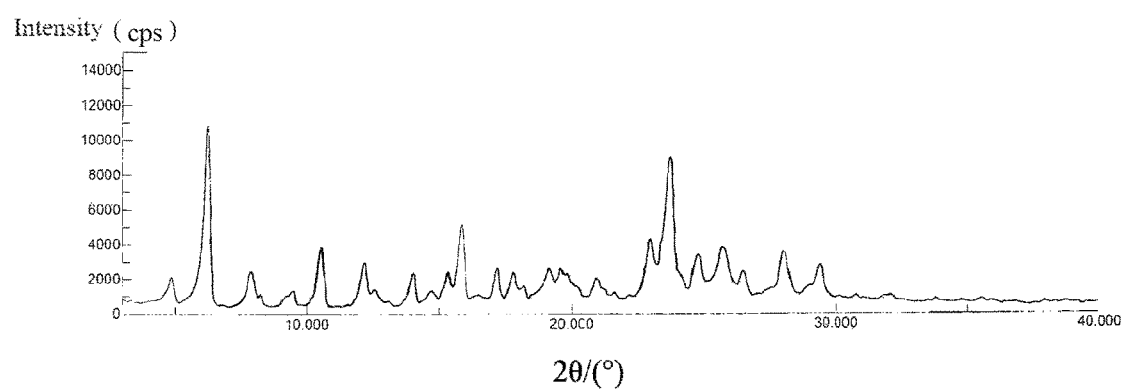
FIG. 2: an X-ray powder diffraction pattern of the crystalline Form B of the compound of Formula 7.

The X-ray powder diffraction pattern of the crystalline Form B of the compound of Formula 7 was shown in FIG. 2.

Example 4: Stability Test

Suitable amounts of the crystalline Form A obtained in Example 2 and the crystalline Form B obtained in Example 3 were taken to carry out experiments on influencing factors according to the methods described in the Chinese Pharmacopoeia, 2010 edition, Part II, Appendix.

The results were shown in Table 1 and Table 2.

TABLE 1

Experiments on influencing factors of the crystalline Form A of the compound of Formula 7

| | | | Light Irradiation | | High-temperature Test | | | | High-humidity Test | |
|---|---|---|---|---|---|---|---|---|---|---|
| | | | Test 4500Lux | | 40° C. | | 60° C. | | 92.5% RH | |
| Test Items | | | | 10 | 5 | 10 | 5 | 10 | | 10 |
| | | 0 day | 5 days | days | days | days | days | days | 5 days | days |
| Relative Substances | Main Peak % | 98.78 | 98.09 | 96.21 | 98.72 | 98.42 | 98.72 | 98.74 | 98.79 | 98.84 |
| | Maximum Single Impurity % | 0.56 | 0.51 | 0.70 | 0.60 | 0.61 | 0.60 | 0.61 | 0.61 | 0.61 |

TABLE 2

Experiments on influencing factors of the crystalline Form B of the compound of Formula 7

| Test Items | | | Light Irradiation Test 4500Lux | | High-temperature Test | | | | High-humidity Test 92.5% RH | |
|---|---|---|---|---|---|---|---|---|---|---|
| | | | | | 40° C. | | 60° C. | | | |
| | | 0 day | 5 days | 10 days | 5 days | 10 days | 5 days | 10 days | 5 days | 10 days |
| Relative Substances | Main Peak % | 99.3 | 98.98 | 98.2 | 99.38 | 99.44 | 99.33 | 99.12 | 99.36 | 99.4 |
| | Maximum Single Impurity % | 0.18 | 0.26 | 0.58 | 0.17 | 0.15 | 0.2 | 0.24 | 0.17 | 0.16 |

What is claimed is:

1. A crystalline Form A of a compound represented by Formula 7,

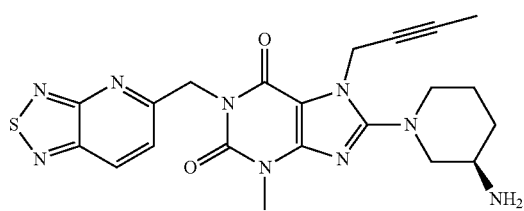

having diffraction peaks at about 6.54, 8.27 and 11.68 degrees 2θ in an X-ray powder diffraction pattern.

2. The crystalline Form A according to claim 1, further having additional diffraction peaks at about 8.67, 9.16, 9.55, 12.17, 12.98, 16.23, 18.15 and 18.91 degrees 2θ.

3. The crystalline Form A according to claim 2, further having additional diffraction peaks at about 10.80, 14.35, 15.05, 15.64, 16.73, 17.31, 19.43, 20.23, 20.79, 21.36, 23.25, 23.96, 24.53, 25.05, 26.54, 28.43, 29.63 and 30.19 degrees 2θ.

4. The crystalline Form A according to claim 1, having a powder X-ray diffraction pattern substantially as shown in FIG. 1.

5. A crystalline Form B of a compound represented by Formula 7,

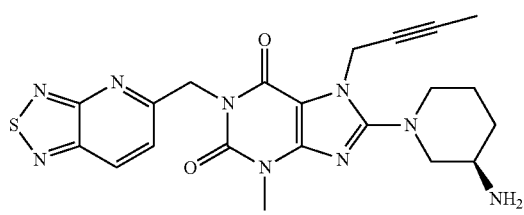

having diffraction peaks at about 4.86, 6.24, 7.88, 10.54, 12.16, 15.82 and 23.70 degrees 2θ in an X-ray powder diffraction pattern.

6. The crystalline Form B according to claim 5, further having additional diffraction peaks at about 9.48, 17.16, 17.76, and 20.94 degrees 2θ.

7. The crystalline Form B according to claim 6, further having additional diffraction peaks at about 12.54, 14.00, 14.68, 15.30, 18.16, 19.16, 19.58, 22.96, 24.76, 25.70, 26.44, 28.02, 28.96 and 29.38 degrees 2θ.

8. The crystalline Form B according to claim 5, having a powder X-ray diffraction pattern substantially as shown in FIG. 2.

9. A crystalline composition, comprising the crystalline Form A according to claim 1, wherein the crystalline Form A according to claim 1 accounts for 50% or more by weight of the crystalline composition.

10. The crystalline composition according to claim 9, wherein the crystalline Form A according to claim 1 accounts for 80% or more by weight of the crystalline composition.

11. The crystalline composition according to claim 9, wherein the crystalline Form A according to claim 1 accounts for 90% or more by weight of the crystalline composition.

12. The crystalline composition according to claim 9, wherein the crystalline Form A according to claim 1 accounts for 95% or more by weight of the crystalline composition.

13. A pharmaceutical composition, comprising the crystalline Form A according to claim 1, and pharmaceutically acceptable adjuvant(s).

14. A crystalline composition, comprising the crystalline Form B according to claim 5, wherein the crystalline Form B according to claim 5 accounts for 50% or more by weight of the crystalline composition.

15. A pharmaceutical composition, comprising the crystalline composition according to claim 9, and pharmaceutically acceptable adjuvant(s).

16. A pharmaceutical composition, comprising the crystalline Form B according to claim 5, and pharmaceutically acceptable adjuvant(s).

17. A method for treating a disease benefiting from DPP-IV inhibition, comprising administering to a subject in need thereof the crystalline Form A according to claim 1; wherein the disease is diabetes.

18. A method for treating a disease benefiting from DPP-IV inhibition, comprising administering to a subject in need thereof the crystalline composition according to claim 9; wherein the disease is diabetes.

19. A method for treating a disease benefiting from DPP-IV inhibition, comprising administering to a subject in need thereof the pharmaceutical composition according to claim 13; wherein the disease is diabetes.

20. A method for treating a disease benefiting from DPP-IV inhibition, comprising administering to a subject in need thereof the crystalline Form B according to claim 5; wherein the disease is diabetes.

* * * * *